United States Patent

Rindt et al.

[11] Patent Number: 5,504,006
[45] Date of Patent: Apr. 2, 1996

[54] ENZYMATIC DETECTION DEVICE FOR DETECTING A GASEOUS OR AEROSOL SUBSTANCE

[75] Inventors: Klaus-Peter Rindt, Lübeck; Stephan Scholtissek, Lübeck, both of Germany

[73] Assignee: Drägerwerk Aktiengesellschaft, Lübeck, Germany

[21] Appl. No.: 448,235

[22] Filed: Dec. 11, 1989

[30] Foreign Application Priority Data

Dec. 17, 1988 [DE] Germany ............... 38 42 607.2

[51] Int. Cl.$^6$ .................................................. C12M 1/34
[52] U.S. Cl. .................. 435/287.7; 435/807; 435/287.9; 435/288.1; 422/56; 422/58
[58] Field of Search .................................. 435/807, 288, 435/291, 296; 436/167, 169, 181; 422/56, 58, 83, 85, 88, 86, 87

[56] References Cited

U.S. PATENT DOCUMENTS

| | | | |
|---|---|---|---|
| Re. 32,016 | 10/1985 | Esders et al. ............... | 435/805 X |
| 4,144,032 | 3/1979 | Davis, Jr. ................... | 23/232 R |
| 4,300,910 | 11/1981 | Pannwitz .................... | 23/232 R |
| 4,315,890 | 2/1982 | Tamers ....................... | 422/58 |
| 4,416,984 | 11/1983 | Wheeler, Jr. ............... | 435/31 |
| 4,525,704 | 6/1985 | Campbell et al. .......... | 340/632 |
| 4,624,929 | 11/1986 | Ullman ....................... | 436/179 |
| 4,743,537 | 5/1988 | McCormick et al. ....... | 435/296 |
| 4,826,759 | 5/1989 | Guire et al. ................ | 422/58 X |

*Primary Examiner*—Jeffrey R. Snay
*Attorney, Agent, or Firm*—Walter Ottesen

[57] ABSTRACT

The invention is directed to a detecting device for detecting gaseous substances and aerosols with the aid of an enzymatic reaction. This reaction takes place between a reactant and an enzyme which, on the one hand, is exposed to the substance to be detected and, on the other hand, is held by a carrier which in the form of a porous holder is in contact with a solution activating and maintaining the enzymatic reaction. The properties of the solution are changed by the enzymatic reaction and are evaluated. The detection device is so improved that a capability for evaluation is made possible which is quantitative and which is specific for a particular substance to be detected. The substance to be detected as a reactant can be stoichiometrically transferrable into a reaction product for quantitatively determining the substance to be detected by means of an enzymatic reaction.

13 Claims, 1 Drawing Sheet

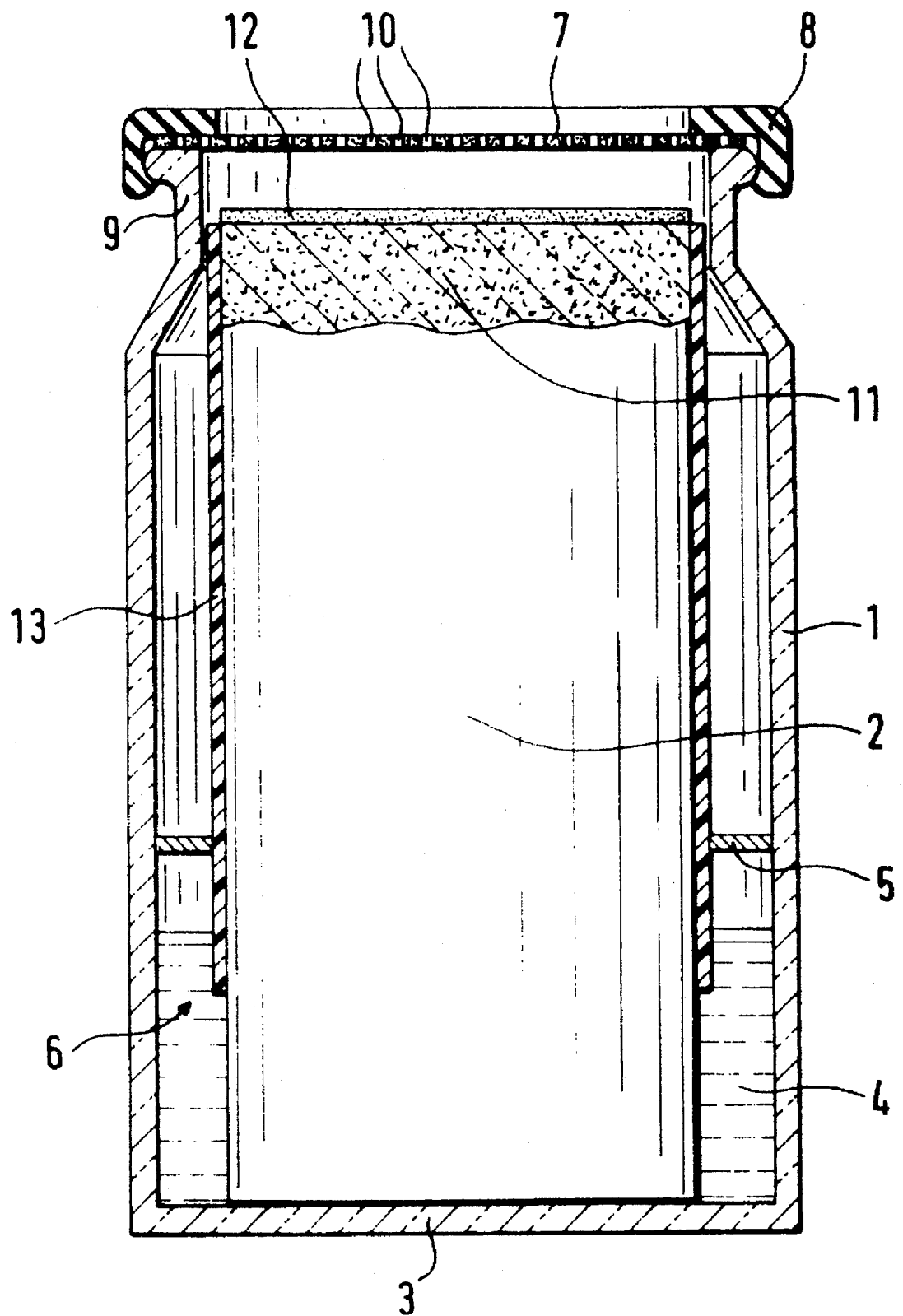

5,504,006

ENZYMATIC DETECTION DEVICE FOR DETECTING A GASEOUS OR AEROSOL SUBSTANCE

FIELD OF THE INVENTION

The invention relates to a detection device for detecting gaseous or aerosol substances with the aid of an enzymatic reaction. The reaction takes place between a reactant and an enzyme which, on the one hand, is subjected to the substance to be detected and, on the other hand, is held by a carrier in the form of a porous holder. The carrier is in contact with a solution which activates and maintains the enzymatic reaction. Property changes of the solution can be evaluated by the enzymatic reaction.

BACKGROUND OF THE INVENTION

An enzymatic sensor for toxic gases is disclosed in U.S. Pat. No. 4,525,704 wherein an enzyme (acetylcholinesterase, AcHe) is covalently bound to a hydrophilic carrier. The enzyme reactant is contained in a pouch and, via the ambient air, is hydrolyzed by the enzyme acting as a catalyst. The reactant is supplied continuously to an enzyme carrier via a filter-membrane combination so that the hydrolysis can take place uninterruptedly as long as no cholinesterase inhibitor is in the ambient to be investigated which would deactivate the enzyme reaction. The hydrolysis is converted to an electrical measuring signal in that the hydrolyzed reactant is oxidized at a measuring electrode.

In this known sensor, acetylthiocholine perchlorate is oxidized to acetic acid and thiocholine perchlorate. The current measured between the measuring electrode and a counter electrode is a measure of the hydrolysis. The enzyme reactant as well as the buffered electrolyte required for the oxidation are contained in a supply reservoir and, via a wick, continuously reach the reactant pouch during operational readiness and measuring time and resupply the reactant pouch with that which has been consumed.

The known sensor tests the ambient air for the presence of such substances which inactivate the enzyme reaction. Such enzyme inhibitors can have different compositions (there are several cholinesterase inhibitors in the cited class of organic phosphorus compounds) so that different inhibitors can be detected only in an unspecific manner by the known sensor. The substance to be detected is itself not the specific enzyme reactant; instead, the enzyme reactant is continuously resupplied by the sensor's own supply means.

SUMMARY OF THE INVENTION

It is an object of the invention to provide a detecting device of the kind described above which is improved so that a detection can be made which is specific for the substance to be detected and which can be evaluated quantitatively.

The detection device of the invention is for detecting a gaseous or aerosol substance. The detection device includes: a porous holder for accommodating an enzyme so as to expose the enzyme to the substance, the enzyme being selected to enter into an enzymatic reaction with the substance acting as a reactant; a solution for activating and maintaining the enzymatic reaction and the solution exhibiting a property change which can be evaluated by means of the enzymatic reaction; and, the porous holder being arranged so as to communicate with the solution for enabling the solution and the enzyme to interact with each other to produce the enzymatic reaction in the presence of the substance to thereby stoichiometrically convert the substance acting as a reactant into a reaction product from which a quantitative determination of the substance is obtained.

The advantage of the invention lies essentially in that the substance to be detected is itself, as a reactant, catalytically converted. In this way, a quantitative determination of a concentration or a dosage of a specific type of gas is possible. The enzyme catalysis now takes place only in the presence of the substance to be detected (acting as a reactant) so that during measurement no enzyme is consumed as is the case for the known sensor.

The reaction product can be used by means of a reaction at the electrodes for an electrical evaluation. This can be done with the aid of suitable electrodes which are in contact with the solution containing the enzyme. The evaluation can, for example, be achieved with a change of the pH-value.

An especially simple evaluation is possible in that the enzyme reaction leads to a colored reaction product. A colored reaction product is formed for such a colorimetric measurement. The colored reaction product is formed by providing that the holder contains an enzyme sensitive to the substance to be detected with the enzyme acting as an enzyme reactant as well as an excess amount of chromogen reagent in solution with the chromogen reagent participating in the reaction. The property changes of the chromogen reagent are recognized in the coloration whose intensity is dependent upon the quantity of the enzyme reactant detected. In this way, a selective colorimetric dosage measurement for toxic gases and aerosols is possible. The evaluation takes place simply by a color comparison with known color standards or, following a completed dosage measurement, by means of a reflectometric evaluation in a laboratory. The detection device is adequate without additional energy supply means and is easily carried and can be utilized over a time duration of several hours by the person carrying the device.

When forming the coloring substance of the enzymatic reaction, either the chromogen reagent itself can color or the chromogen reagent can form a coloring substance with a further coloring substance precursor after a completed reaction. The course of the enzymatic reaction is so rapid that the enzyme simply operates as a biocatalyst in the presence of an enzyme reactant in order to generate a coloring substance.

In an advantageous embodiment of the invention, the porous holder can be a translucent charge of a cuvette which contains the reagent solution with the enzyme and communicates with the ambient via an opening of the cuvette which is permeable for the substance to be detected as a reactant. A badge-shaped or tube-shaped colorimetric dosimeter is obtained in a simple manner which colors when exposed to the substance to be detected.

A likewise advantageous embodiment is provided in that the reagent solution is contained in a separate reservoir wherein a wick containing the enzyme is dipped. With this embodiment, the condition is achieved that the color reaction only takes place when the porous body with its carrier containing the enzyme is brought into contact with the reservoir. No enzymatic reaction takes place as long as this contact is not provided. A detection device configured in this manner has a longer shelf life since the enzyme is only activated after the reaction solution is made available.

The propagation of the color reaction is limited to the surface of the carrier since the capillary force of the solution rising up from the reservoir prevents a back diffusion in the wick. Accordingly, no color diminution by coloring substances which diffuse away takes place. The concentration of the formed coloring substance on the surface of the enzyme carrier facilitates the visual evaluation of the color intensity change. By preventing the back diffusion of the coloring substance, also those chromogen reagents can be utilized which form a soluble coloring substance. In this way, the selection of possible coloring substances which can be used is no longer limited to insoluble coloring substances. This fact expands the area of use of the dosimeter to the detection of a plurality of toxic gases and/or aerosols.

The end of the porous body which faces toward the substance to be detected is a simple location where the enzyme can be provided. The enzyme is advantageously applied in lyophilic form (or also absorbant or covalent) at the end of the porous body which acts as the carrier for the enzyme. The solution from the reservoir rises in the porous body and activates the enzyme located at the end of this body and concentrates the enzyme at the surface. A back diffusion into the porous body is prevented by the capillary force of the rising solution. The formed soluble as well as insoluble coloring substances remain also on the thin surface layer of the porous body and are therefore especially accessible for visual evaluation. The solution in the reservoir can be separately prepared and stored and the porous body is brought into contact with the reservoir only when required whereby the detection reaction is initiated at the end of the porous body facing toward the substance to be detected.

A further advantageous possibility for applying the enzyme to a carrier is, for example, to covalently bind it to a membrane covering the porous body.

A suitable porous body is a porous glass rod having planar surfaces at its ends and having a typical length of 20 mm and a diameter of 6 mm. Such glass rods are positioned in suitable glass vessels forming reservoirs and the glass vessels have an inner diameter of 8 mm and a height of 24 mm. The solution with the reagents or also together with the enzyme is filled into the glass vessel. The porous glass rod is dipped into the reservoir and draws the solution up via capillary action and brings it to the surface of the glass rod facing the substance to be detected. At this surface, the enzyme can react with an enzyme reactant which is present and lead to a coloration of the coloring precursors present in the solution.

An especially advantageous preparation of the detection device is obtained in that the enzyme is taken up at the end to be exposed to the substance to be detected and the reagents are taken up in lyophilic form at the end of the porous body facing away from the substance to be detected. The enzyme and the reagents are capable of the enzymatic reaction after contact is made to the reservoir which contains the solutizing agents for mobilizing the lyophilic reactants. In this way, the porous carrier as the carrier for the enzyme, on the one hand, and the reagents required for the enzymatic reaction, on the other hand, are accommodated at spatially different locations. In the manner described above, the enzymatic reaction remains inactive until the porous body is dipped into the reservoir which contains the solutizing agents which mobilize the lyophilic reactant. Only thereafter is the detection device ready for a dosimetric measurement. Detergents containing groups of cationically active, anionically active or non-ionogenic tensides are suitable as solutizing agents. Such detergents are, for example, known under the trade name TRITON.

An increased consumption of the reactant participating in the enzymatic reaction takes place if a large quantity of the substance to be detected is collected over a long time duration. This would lead to an unwanted early exhaustion of the detection device so that it is advantageous to cover the porous body with a gas-permeable membrane with respect to the ambient containing the substance to be detected. The membrane then acts as a diffusion barrier and determines the accessibility of the enzyme reactant to the enzyme. In this way, a dosimetry for higher concentrations can be carried out over a longer time duration. These concentrations would otherwise lead to a deep coloration which could not be further evaluated.

On the other hand, a long duration measurement can be carried out at high concentrations of the substance to be detected with a coloring reagent which provides only a slight coloration depth. With a suitable composition of enzyme and coloring reagents, a long duration measurement as well as a short duration measurement can be realized in one and the same detection device when a porous body having the above-mentioned cover membrane is combined with a porous body having no covering membrane. The two porous bodies are dipped into corresponding ones of the separated reservoirs containing the different solutions.

For detecting, for example, hydrogen peroxide as the reactant for the enzyme horseradish peroxidase, a solution of 1 mMol/l 4-aminoantipyrine and 1 mMol/l of N-ethyl-N-sulphopropyl-m-toluidine is prepared in a 50 mMol/l phosphate buffer as coloring reagents. The phosphate buffer is intended to guarantee a pH-value of 7.3. With this type of formulation, hydrogen peroxide is selectively detectable via the peroxidase (POD) as a biocatalyst by means of the color reaction. The chromogens are formed by aminoantipyrine and ethyl-sulphopropyltoluidine and these chromogens combine to a coloring substance because of the enzyme reaction.

The detection of hydrogen peroxide with a chromogen as a coloring reagent, which is directly converted into a coloring substance because of the enzyme reaction, occurs by means of a solution which contains two international units of the enzyme horseradish peroxidase (POD) as well as a coloring reagent in the form of a millimolar 2.2' acino-bis-(3-ethylbenzthiazoline-6-sulphonic acid) in a 0.1 molar TRIS-HCl-buffer pH 8.0.

Further examples for detecting gases by means of an enzymatic reaction are described below.

For the long-term measurement of hydrogen peroxide, a less sensitive coloring system is used such as a solution of 1 mMol/l 4-chlorine-1-naphthol in 50 mMol/l TRIS-HCl and 0.2 Mol/l sodium chloride solution.

Acetaldehyde is measured with aldehydedehydrogenase (AlDH) in such a manner that first the enzyme is freed of stabilizers producing blind reactions in that it is precipitated with ammonium sulphate and is absorbed in 0.1 molar potassium phosphate buffer pH 8.0. A porous glass rod is moistened at its one end with 0.05 ml of a solution of diaphorase (4 milliunits per ml) and ALDH (3 milliunits per ml) in the same buffer and the opposite end is dipped into a glass vessel defining a reservoir. The reservoir contains 0.3 ml of a solution having 0.1 N-potassium phosphate pH 9.0, 1.6 mMol/l nicotineamide-adenine-dinucleotide (AND) and 0.3 millimoles iodine-nitrotetrazoliumchloride (INT). When the porous glass rod is exposed to an atmosphere containing acetaldehyde, concentrations of less than 5 to 100 ppm of acetaldehyde can be detected after an exposure time of 5 minutes.

For determining formaldehyde with formaldehydedehydrogenase, the enzyme is dissolved in 50 mMol/l phosphate buffer pH 7.4 (10 U/ml). Porous glass rods are dipped for a short time into the enzyme solution and are dried in the air for 10 minutes. The end facing toward the substance to be detected is surrounded with a silicon sleeve having a length of approximately 10 mm. Thereafter, the rod is placed with its other end in a glass vessel having a height of approximately 24 mm. The glass vessel contains a solution having the following composition: 50 mMol/l phosphate buffer pH 7.4; 0.2 mMol/l INT; 0.05 mMol/l methoxyphenazine methosulphate; 1 mMol/l NAD. In this way, formaldehyde in the gas phase can be detected after an exposure time of approximately 10 minutes at a concentration of less than 1 ppm.

BRIEF DESCRIPTION OF THE DRAWING

The invention will now be described with reference to the drawing wherein the single figure is a schematic of a detecting device according to the invention.

DESCRIPTION OF THE PREFERRED EMBODIMENTS OF THE INVENTION

A glass vessel 1 is open at one end and receives the cylindrical porous body 2 which extends from the opening of the glass vessel 1 to the base 3 thereof. The porous body 2 is likewise made of glass and dips into the solution 4 with its end facing toward the base 3. The solution 4 contains the reagents necessary for the enzymatic reaction such as coloring precursors and cofactors in a buffer solution. The solution 4 is contained in a reservoir 6 partitioned by an annularly shaped collar 5. The collar 5 is attached along the inner wall surface of the vessel 1 and, on the one hand, prevents the solution 4 from escaping from the vessel 1 and, on the other hand, acts to hold the porous body 2 in its position.

The opening of the glass vessel 1 is closed by a porous membrane 7 which acts as a diffusion barrier. A rubber elastic collar 8 fixes the membrane 7 about a protrusion 9 of the vessel opening. The end 11 of the porous glass rod 2 facing toward the pore openings 10 of the membrane 7, and therefore toward the ambient containing the substance to be detected, is closed off by a membrane 12 which functions as a carrier for the covalently bound enzyme. A silicon sleeve 13 is pulled over the surface of the glass rod 2 at least outside of the reservoir 6 to improve the capillary diffusion of the solution 4 from the reservoir 6 to the carrier 12. The silicon sleeve 13 extends beyond the collar 5 into the reservoir whereby it also provides a sealing function for the reservoir 6.

It is understood that the foregoing description is that of the preferred embodiments of the invention and that various changes and modifications may be made thereto without departing from the spirit and scope of the invention as defined in the appended claims.

What is claimed is:

1. A detection device for detecting a specific gaseous or aerosol substance defining an enzyme substrate, the detection device comprising:

a vessel defining an interior;

an enzyme;

a holder holding said enzyme and having an upper surface exposed to said substance;

an aqueous buffer solution held in said interior of said vessel;

a chromogen reagent disposed in said holder;

said holder having a lower surface immersed in said solution and being porous to facilitate the capillary transport of said solution into and along said holder to bring said enzyme to said upper surface where said solution prepares said enzyme to act as a catalyzer for facilitating a reaction involving at least said enzyme substrate and said chromogen reagent to thereby form a product having a coloration with an intensity dependent upon the quantity of the substance detected;

said chromogen reagent being disposed in said holder in lyophilic form below said upper surface.

2. A detection device for detecting a specific gaseous or aerosol substance defining an enzyme substrate, the detection device comprising:

a vessel defining an interior;

an enzyme;

a holder holding said enzyme and having an upper surface exposed to said substance;

an aqueous buffer solution held in said interior of said vessel and containing a chromogen reagent;

said holder having a lower surface immersed in said solution and being porous to facilitate the capillary transport of said solution into and along said holder to bring said enzyme to said upper surface where said solution prepares said enzyme to act as a catalyzer for facilitating a reaction involving at least said enzyme substrate and said chromogen reagent to thereby form a product having a coloration with an intensity dependent upon the quantity of the substance detected.

3. The detection device of claim 2, said chromogen reagent being present in said solution and said solution further containing at least one additional substance in the form of a cofactor reagent which together form a coloring after said reaction is completed.

4. The detection device of claim 2, said porous holder having an end portion facing toward the substance to be detected and said end portion accommodating said enzyme.

5. The detection device of claim 2, comprising a porous diffusion membrane for covering said porous holder with respect to the ambient containing said substance.

6. The detection device of claim 2, wherein the substance to be detected is hydrogen peroxide and the enzyme is horseradish peroxidase for which said solution contains 1 mMol/l 4-aminoantipyrine and 1 mMol of N-ethyl-N-sulphopropyl-m-toluidine in 50 mMol/l phosphate buffer pH-value 7.3 as coloring reagents and 2 Units peroxidase per ml.

7. The detection device of claim 2, wherein the substance to be detected is hydrogen peroxide for which said solution contains 2 Units (international units) of the enzyme horseradish peroxidase per ml and as a coloring reagent one mMol/l 2.2-acino-bis-(3-ethylbenzthiazoline-6-sulphonic acid) in 0.1 Mol/l of TRIS-HCl-buffer pH 8.0.

8. A detection device for detecting a specific gaseous or aerosol substance defining an enzyme substrate, the detection device comprising:

a vessel defining an interior;

an enzyme;

a holder having an upper surface;

an aqueous buffer solution held in said interior of said vessel and containing a chromogen reagent;

a porous membrane covering said upper surface and exposed to said substance to be detected;

said enzyme being bound to said porous membrane;

said holder having a lower end communicating with said solution and said upper surface facing away from said solution and toward said membrane;

said holder being porous to facilitate the capillary transport of said solution into and along said holder to bring said solution into contact with said membrane to activate said enzyme so as to permit said enzyme to act as a catalyzer for facilitating a reaction involving at least said enzyme substrate and said chromogen reagent to thereby form a product having a coloration having an intensity dependent upon the quantity of the substance detected.

9. The detection device of claim 8, said chromogen reagent being present in said solution and said solution further containing at least one additional substance in the form of a cofactor reagent which together form a coloring after said reaction is completed.

10. The detection device of claim 8, said reagents being accommodated in said holder in lyophilic form below said upper surface; said interior defining a reservoir for containing solutizing agents for mobilizing the lyophilic reaction partners; said enzyme being made capable of said enzymatic reaction after a connection is established between the porous holder and said reservoir.

11. The detection device of claim 8, comprising a porous diffusion membrane for covering said porous holder with respect to the ambient containing said substance.

12. The detection device of claim 8, wherein the substance to be detected is hydrogen peroxide and the enzyme is horseradish peroxidase for which said solution contains 1 mMol/l 4-aminoantipyrine and 1 mMol of N-ethyl-N-sulphopropyl-m-toluidine in 50 mMol/l phosphate buffer pH-value 7.3 as coloring reagents and 2 Units peroxidase per ml.

13. The detection device of claim 8, wherein the substance to be detected is hydrogen peroxide for which said solution contains 2 Units (international units) of the enzyme horseradish peroxidase per ml and as a coloring reagent one mMol/l 2.2-acino-bis-(3-ethylbenzthiazoline-6-sulphonic acid) in 0.1 Mol/l of TRIS-HCl-buffer pH 8.0.

* * * * *